United States Patent [19]

Takase et al.

[11] Patent Number: 4,752,320

[45] Date of Patent: Jun. 21, 1988

[54] METHOD FOR CONTROLLING THE GROWTH OF WEEDS

[75] Inventors: Masayuki Takase, Takarazuka; Yoshimi Yamada, Nishinomiya; Mitsuru Sasaki, Toyonaka, all of Japan

[73] Assignee: Sumitomo Chemical Company, Limited, Osaka, Japan

[21] Appl. No.: 853,037

[22] Filed: Apr. 17, 1986

[30] Foreign Application Priority Data

Apr. 18, 1985 [JP] Japan ................................. 60-83502

[51] Int. Cl.$^4$ ........................................... A01N 57/12
[52] U.S. Cl. ..................................................... 71/86
[58] Field of Search ............................................ 71/86

[56] References Cited

U.S. PATENT DOCUMENTS 4,473,561 9/1984 Ishiguri et al. ..................... 424/211

FOREIGN PATENT DOCUMENTS 0002031 5/1979 European Pat. Off. .
0063464 10/1982 European Pat. Off. .
0115466 8/1984 European Pat. Off. .

OTHER PUBLICATIONS

Par M. J. Ville, Annales de Chimie, et de Physique, 23, 289–362, 1981.

Primary Examiner—Catherine L. Mills
Attorney, Agent, or Firm—Birch, Stewart, Kolasch & Birch

[57] ABSTRACT

A method for controlling the growth of undesired weeds is disclosed. The method includes applying a herbicidally effect amount of a herbicidal composition which contains as an essential active ingredient a compound of the formula:

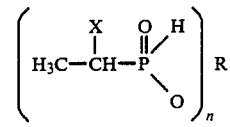

wherein X is a hydroxyl group or a hydroxylamino group, R is a hydrogen atom, an inorganic counter cation, an an organic counter cation or an ester residue, and n is an integar of 1 to 3, and an inert carrier or diluent, to the area where the weeds grow or will grow.

5 Claims, No Drawings

METHOD FOR CONTROLLING THE GROWTH OF WEEDS

The present invention relates to a herbicide comprising α-substituted ethyl phosphinic acid or derivatives thereof having the formula [I]

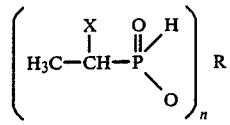

wherein X is a hydroxyl group or a hydroxylamino group; R is a hydrogen atom, an inorganic or organic counter cation or an ester residue; and n is an integer of 1 to 3.

The compound [I], wherein X=OH, R=H and n=1, is disclosed in Annales de Chimie et de Physique, 23, 289–362, 1891, J. Ville and is prepared by known processes. U.S. Pat. No. 4,473,561 discloses that α-hydroxyethyl phosphinic acid and α-(hydroxylamino)ethyl phosphinic acid are useful as a bacetericide in the agricultural field. However, these references do not refer to herbicidal activity of the present compound [I]. The present inventors have first discovered the herbicidal activity of the compound [I].

The inorganic counter cations include, for example, alkaline earth metal cations such as calcium (II), magnesium (II), and barium (II); alkali metal cations such a sodium (I) and potassium (I), and heavy metal cations such as iron (III), copper (II), zinc (II) and manganese (II). The organic counter cations include, for example, alkoxy(lower)alkylammonium, aralkylammonium and alkylammonium. The ester residues are, for example, alkyl groups, halo(lower)alkyl groups, alkoxy(lower)alkyl groups, alkylthio(lower)alkyl groups and substituted or unsubstituted aralkyl group.

The terms "alkyl" and "alkoxy" mean those having not more than 13 carbon atoms. The term "lower" means not more than 8, preferably not more than 4. The term "halo" encompasses chlorine, bromine and fluorine.

The "aralkyl" includes, for example, benzyl, phenethyl, naphthyl($C_1$–$C_2$)alkyl and anthranylmethyl, and the terms "substituted aralkyl" include halobenzyl, $C_1$–$C_4$ alkylbenzyl, $C_1$–$C_4$ alkoxybenzyl, phenoxybenzyl, phenylbenzyl, halophenethyl, $C_1$–$C_4$ alkylphenethyl, $C_1$–$C_4$ alkoxyphenethyl, halonaphthyl(-$C_1$–$C_2$)alkyl, $C_1$–$C_4$ alkylnaphthyl($C_1$–$C_2$)alkyl, $C_1$–$C_6$-alkoxynaphthyl ($C_1$–$C_2$)alkyl.

Preferred compounds are those where X is a hydroxyl group, preferably X=OH and R is a hydrogen atom, calcium (II), magnesium (II), barium (II), iron (III), copper (II), zinc (II), manganese (II), $C_1$–$C_{10}$ alkoxy ($C_1$–$C_3$)alkylammonium, naphthyl($C_1$–$C_2$)alkylammonium, $C_1$–$C_6$ alkyl group, chloro($C_1$–$C_2$)alkyl group, $C_1$–$C_2$ alkylthiomethyl group or dichlorobenzyl group. More preferred compounds are 2-hydroxyethylphosphinic acid, calcium bis(2-hydroxyethylphosphinate), (+)-2-hydroxyethylphosphinic acid, (−)-2-hydroxyethylphosphinic acid, calcium bis[(+)-2-hydroxyethylphosphinate] and calcium bis[(−)-2-hydroxyethylphosphinate].

The present invention includes all optical isomers and geometerical isomers of the compound [I].

Embodiments of the compound [I] are illustratively shown below, however, they are not intended to be limit the present invention.

TABLE 1

Formula

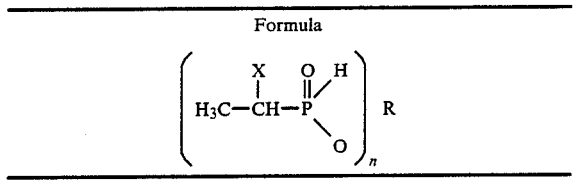

| Compound No. | R | X | n | Physical property |
|---|---|---|---|---|
| (1) | (n)$C_3H_7$ | OH | 1 | $n_D^{20}$ 1.4535 |
| (2) | (n)$C_5H_{11}$ | OH | 1 | $n_D^{20}$ 1.4505 |
| (3) | (iso)$C_5H_{11}$ | OH | 1 | $n_D^{21}$ 1.4505 |
| (4) | (n)$C_6H_{13}$ | OH | 1 | $n_D^{20}$ 1.4515 |
| (5) | $CH_2CH_2Cl$ | OH | 1 | $n_D^{18}$ 1.4743 |
| (6) | $CH_2CH_2SCH_3$ | OH | 1 | $n_D^{20.0}$ 1.4980 |
| (7) | $CH_2$—C$_6$H$_3$Cl$_2$ | OH | 1 | $n_D^{20}$ 1.5537 |
| (8) | $^+H_3NC_3H_6OC_{10}H_{21}$ | OH | 1 | Resinous |
| (9) | $^+H_3N$—$C(CH_3)$—naphthyl | OH | 1 | mp 164° C. |
| (10) | $Ca^{2+}$ | OH | 2 | mp 150° C. (decomp.) |
| (11) | $Cu^{2+}$ | OH | 2 | mp 105° C. (decomp.) |
| (12) | $Fe^{3+}$ | OH | 3 | mp 205° C. (decomp.) |
| (13) | $Zn^{2+}$ | OH | 2 | mp 130° C. (decomp.) |
| (14) | $Mg^{2+}$ | OH | 2 | mp 120° C. (decomp.) |
| (15) | $Mn^{2+}$ | OH | 2 | mp 140° C. (decomp.) |
| (16) | $Ba^{2+}$ | OH | 2 | mp 115° C. (decomp.) |
| (17) | H | NHOH | 1 | mp 95–100° C. |
| (18) | H | OH | 1 | $n_D^{23}$ 1.4780 |

| Compound No. | Compound | Physical property |
|---|---|---|
| (19) |  | $[\alpha]_D^{25}$ +11.2°($H_2O$) |
| (20) |  | $[\alpha]_D^{25}$ −10.8°($H_2O$) |
| (21) |  | $[\alpha]_D^{25}$ +12.0°($H_2O$) |

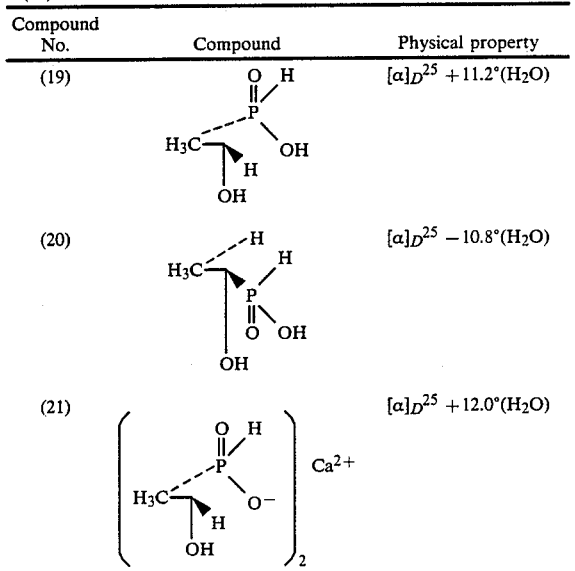

TABLE 1-continued

Formula $$\left(\begin{array}{c} X \quad O \quad H \\ | \quad \| \diagup \\ H_3C-CH-P \\ \diagdown O \end{array}\right)_n R$$

(22)
$$\left(\begin{array}{c} \diagup H \\ H_3C \diagdown \diagup H \\ P \\ \| \diagdown \\ O \quad O^- \\ OH \end{array}\right)_2 Ca^{2+}$$
$[\alpha]_D^{25} -11.2°(H_2O)$ The herbicidal composition of the present invention exhibits a high herbicidal activity against a wide variety of weeds including broad-leaved weeds, Graminaceous weeds and Cyperaceous weeds in agricultural plowed fields by foliar or soil treatment, especially by foliar treatment, without producing any material phytotoxicity on various agricultural crops as mentioned below.

| Japanese | English | Scientific name |
|---|---|---|
| Toomorokoshi | Corn, (Maize) | Zea mays |
| Wata | Cotton | Gossypium hirsutum |
| Tensai | Sugar beet | Beta vulgaris |

Listed below are examples of weeds to which the herbicidal compositions of the present invention exert herbicidal activity.

| | Weeds on Plowed Field Broad-leafed weeds | |
|---|---|---|
| Japanese | English | Scientific name |
| Sobakazura | Wild buckwheat | Polygonum convolvulus |
| Suberihiyu | Common purslane | Portulaca oleracea |
| Shiroza | Common lambsquarters | Chenopodium album |
| Aogeitoo | Redroot pigweed | Amaranthus retroflexus |
| Daikon | Radish | Raphanus sativus |
| Noharagarashi | Wild mustard | Sinapis arvensis |
| Amerika-tsunokusanemu | Hemp sesbania | Sesbania exaltata |
| Ebisugusa | Sicklepod | Cassia obtusifolia |
| Ichibi | Velvetleaf | Abutilon theophrasti |
| Amerika-kingojika | Prickly sida | Sida spinosa |
| Amerikaasagao | Ivyleaf morningglory | Ipomoea hederacea |
| Marubaasagao | Tall morningglory | Pharbitis purpurea |
| Seiyoohirugao | Field bindweed | Convolvulus arvensis |
| Inukamitsure | Scentless chamomile | Matricaria perforata |
| Sanaetade | Pale smartweed | Polygonum lapathifolium |
| Nazuna | Shepherdspurse | Capsella bursa-pastoris |
| Onamomi | Common cocklebur | Xanthium strumarium |
| Butakusa | Common ragweed | Ambrosia artemisii-folia |
| Himawari | Common sunflower | Helianthus annuus |
| Corn marigold | Corn marigold | Chrysanthemum segetum |
| Gramineous weeds | | |
| Hie | Japanese millet | Echinochloa frumentacea |
| Inubie | Barnyardgrass | Echinochloa crus-galli |
| Enokorogusa | Green foxtail | Setaria viridis |
| Mehishiba | Large crabgrass | Digitaria sanguinalis |
| Suzumenokatabira | Annual bluegrass | Poa annua |
| Nosuzumenoteppo | Blackgrass | Alopecurus myosuroides |
| Enbaku | Oats | Avena sativa |
| Karasumugi | Wild oats | Avena fatua |
| Seibanmorokoshi | Johnsongrass | Sorghum halepense |
| Shibamugi | Quackgrass | Agropyron repens |
| Umanochahiki | Downy brome | Bromus tectorum |
| Gyoogishiba | Bermudagrass | Cynodon dactylon |
| Cyperaceous Weeds | | |
| Kogomegayatsuri | Rice flatsedge | Cyperus iria |
| Hamasuge | Purple nutsedge | Cyperus rotundus |

The herbicidal composition of the present invention may be formulated in any composition form, such as an emulsifiable concentrate, wettable powder, suspension, granule, water soluble composition, liquid composition, etc. by mixing with a solid carrier, liquid carrier, surface active agent and other formulation adjuvants.

In the composition, the compound (I) is contained as active ingredient therein in the range of 1-95% by weight, preferably 2-80% by weight.

Examples of the solid carrier are kaolin clay, attapulgite clay, bentonite, terra alba, pyrophyllite, talc, diatomaceous silica, calcite, walnut powder, urea, ammonium sulfate, synthetic hydrated silicon dioxide and like fine powders or particles. As the liquid carrier or diluent, there may be exemplified aromatic hydrocarbons, e.g. xylene, methylnaphthalene, alcohols, e.g. isopropanol, ethylene glycol, cellosolve, ketones, e.g. acetone, cyclohexanone, isophorone, vegetable oils, e.g. soybean oil, cotton seed oil, dimethylsulfoxide, acetonitrile and water.

The surface active agent used for emulsification, dispersion or spreading may be any of the anionic and nonionic type of agents. Examples thereof include the anionic type agent such as alkylsulfates, alkylsulfonates, alkylarylsulfonates, dialkylsulfosuccinates, phosphates of polyoxyethylenealkylaryl ethers, and the nonionic type agent such as polyoxyethylene alkyl ethers, polyoxyethylene alkylaryl ethers, polyoxyethylene polyoxypropylene block copolymer, sorbitan fatty acid esters, polyoxyethylene sorbitan fatty acid esters, etc.

Examples of formulation adjuvants include ligninsulfonates, alginate, polyvinyl alcohol, gum arabic, CMC (carboxymethyl cellulose) or PAP (isopropyl acid phosphate), etc.

Practical embodiments of the herbicidal composition according to the present invention are illustratively shown in the following examples wherein parts are by weight. The compound number of the active ingredient corresponds to the one in Table 1.

FORMULATION EXAMPLE 1

50 parts of compound No. 22 as an active ingredient, 3 parts of calcium ligninsulfonate, 2 parts of sodium laurylsulfate and 45 parts of synthetic hydrated silicon dioxide are well mixed while being powdered to obtain a wettable powder.

FORMULATION EXAMPLE 2

10 parts of compound No. 18, 14 parts of polyoxyethylenestyryl phenyl ether, 6 parts of calcium dodecylbenzenesulfonate and 70 parts of cyclohexanone are well mixed to obtain an emulsifiable concentrate.

FORMULATION EXAMPLE 3

2 parts of compound No. 10, 1 part of synthetic hydrated silicon dioxide, 2 parts of calcium ligninsulfonate, 30 parts of bentonite and 65 parts of kaolin clay are well mixed while being powdered. The mixture is then kneaded with water, granulated and dried to obtain granules.

FORMULATION EXAMPLE 4

25 parts of compound No. 22, 3 parts of polyoxyethylene sorbitan molooleate, 3 parts of CMC and 69 parts of water are well mixed and pulverized until the particle size of the powders becomes less than 5 microns to obtain a suspension.

FORMULATION EXAMPLE 5

10 parts of the compound No. 21, 1 part of polyoxyethylenestyryl phenyl ether and 89 parts of water are well mixed to obtain a liquid composition.

The herbicidal composition of the present invention thus formulated in any suitable composition form is useful for the pre- or post-germination control of undesired weeds by means of soil or foilar treatment. These treatments include the application to the soil surface prior or subsequent to planting, and the incorporation into the soil. The foliar treatment may be effected by spraying the herbicidal composition over the top of plants. Otherwise it may be applied directly to weeds if care is taken to keep the chemical off the crop foliage.

The herbicidal composition may be used in a mixture or blend of some other herbicide to improve activity, and in some cases, a synergistic effect can be expected. Further, they may be applied in combination with insecticides, acaricides, nematocides, fungicides, plant growth regulators, fertilizers, soil improvers, etc.

Furthermore, the herbicidal composition of the present invention can be used for agricultural plowed fields, orchards, pasture lands, lawns, forests, non-agricultural fields, etc.

Use as Herbicides

The dosage rate of the compound (I) which is an active ingredient of the herbicidal composition in the present invention may vary depending on prevailing weather conditions, the site conditions, formulations used, the prevailing season, the mode of application, the soil involved, the crop and weed species, etc. Generally, however, the dosage rate is from 1 to 500 g, preferably from 5 to 500 g of the active ingredient per are. The herbicidal composition formulated in the form of an emulsifiable concentrate, liquid composition, a wettable powder or a suspension may ordinarily be employed by diluting it with water at a volume of 1 to 10 liters per are, if necessary, with the addition of an adjuvant such as a spreading agent. The herbicidal composition formulated in the form of a granule may be normally applied as such without dilution. Examples of the spreading agent include, in addition to the surface active agents as noted above, polyoxyethylene resin acid (ester), ligninsulfonate, abiethylenic acid salt, dinaphthylmethane disulfonate, paraffin, etc.

In the following, the biological data of the herbicidal composition of the present invention are illustratively shown in the test examples, wherein an active compound [I] is noted by the compound number listed in Table 1. The compounds shown in Table 2 below were used for comparison.

TABLE 2

| Compound No. | Chemical structure | Note |
| --- | --- | --- |
| A | $[H_5C_2O-\underset{\underset{O^-}{\mid}}{P}(=O)-\underset{}{C}(=O)-NH_2]\ NH_4^+$ | Fosamine ammonium |
| B | $H_3CCH(NH_2)-P(=O)(H)(OH)$ | EP0002031A |

The phytotoxicity to crop plants and the herbicidal activity on weeds were observed visually in terms of the degree of germination as well as the growth inhibition and rated with a ranking index in any of 0, 1, 2, 3, 4 or 5, in which the numeral "0" indicates that no material difference is observed in comparison with the untreated plant and the numeral "5" indicates the complete inhibition or death of the test plants.

TEST EXAMPLE 1

Soil treatment, admixing into the soil of a plowed field.

Soil of a plowed field was filled in cylindrical plastic pots of diameter-10 cm, height-10, cm and thereon seeds of Tall morningglory (Marubaasagao), Velvetleaf (Ichibi), were sowed and covered with soil. Then a designated amount of the test compound, which had been formulated into an emulsifiable concentrate according to Formulation Example 2 and diluted with water comparable to a volume of 10 liters per are, was sprayed by a small sprayer over the surface of the soil in pots. Thereafter the surface soil for 4 cm in depth was well blended. Furthermore, a tuber of Purple nutsedge (Hamasuge) was buried in 2 cm depth. After treatment, test plants were cultivated in a greenhouse for 20 days subsequent to the soil treatment above while the herbicidal activity was examined. The results are shown in Table 3.

TABLE 3

| Test compound | Dosage of active ingredient (g/a) | Herbicidal activity | | |
| --- | --- | --- | --- | --- |
| | | Purple nutsedge | Tall morningglory | Velvetleaf |
| (1) | 80 | — | 4 | 4 |
| (2) | 80 | 4 | — | — |
| (3) | 80 | 4 | — | — |
| (4) | 80 | — | 4 | 4 |
| (5) | 80 | — | 4 | 4 |
| (7) | 80 | 4 | 4 | 4 |
| (10) | 80 | — | 4 | — |
| (11) | 80 | 4 | — | — |
| (17) | 80 | — | 5 | 4 |
| (18) | 80 | — | 5 | 5 |
| (19) | 80 | — | 5 | — |
| (20) | 80 | — | 5 | 5 |
| A | 80 | — | 0 | 0 |
| B | 80 | 1 | 1 | 1 |

TEST EXAMPLE 2

Foliar treatment, plowed field.

Cylindrical plastic pots of diameter-10 cm, height-10 cm were filled with soil of a plowed field and seeds of Japanese millet (Hie), Oats (Enbaku), Radish (Daikon), and Velvetleaf (Ichibi) were sowed and cultivated for 10 days in a greenhouse. Thereafter a designated amount of the test compound, which had been formulated into an emulsifiable concentrate according to Formulation Example 2 and diluted with water containing a spreading agent comparable to 10 liters per are, was sprayed by a small sprayer over the top of the weeds to effect the foilar treatment. Treated weeds were cultivated in a greenhouse for an additional 20 days subsequent to the treatment while the herbicidal activity was examined. The results are shown in Table 4.

TABLE 4

| Test compound | Dosage of active ingredient (g/a) | Herbicidal activity | | | |
|---|---|---|---|---|---|
| | | Japanese millet | Oats | Radish | Velvetleaf |
| (3) | 80 | 5 | 5 | — | 5 |
| (8) | 80 | — | 4 | — | 4 |
| (9) | 80 | 4 | 4 | — | — |
| (10) | 80 | — | 4 | — | 4 |
| (11) | 80 | — | — | — | 4 |
| (16) | 80 | — | 4 | — | 4 |
| (17) | 80 | 5 | 5 | — | 5 |
| (18) | 80 | 5 | 5 | 5 | 5 |
| (19) | 80 | 5 | 4 | 5 | 5 |
| (20) | 80 | 4 | 5 | 5 | 5 |
| (22) | 80 | 5 | 5 | — | 4 |
| A | 80 | 0 | 0 | 0 | 0 |

TEST EXAMPLE 3

Foliar treatment, plowed field.

Vats measuring area 33×23 cm² and depth 11 cm were filled with soil of a plowed field, where Corn (Toomorokoshi), Cotton (Wata), Sugar beet (Tensai), Oats (Embaku), Johnsongrass (Seibanmorokoshi), Japanese millet (Hie), Large crabgrass (Mehishiba), Green foxtail (Enokorogusa), Common cocklebur (Onamomi), Velvetleaf (Ichibi), and Tall morningglory (Marubasaagao) were sowed and cultivated for 18 days. Thereafter a designated amount of the test compound, which had been formulated into an emulsifiable concentrate according to Formula Example 2 and diluted with water containing a spreading agent comparable to 5 liters per are, was sprayed by a small sprayer over the top of the weeds to effect the foliar treatment equally on the whole surface. At this time, growth conditions of weeds and crops depend on the kinds of grass and the height of grass is 4 to 20 cm at 1 to 5 leaf stages. The herbicidal activity was examined after 20 days of treatment. The results are shown in Table 5. This test was carried out in a greenhouse for the whole time.

Soil of a plowed field was filled in cylindrical plastic pots of diameter-10 cm, height-10 cm and thereon a tuber of Purple nutsedge (Hamasuge) was transplanted and cultivated for 28 days in a greenhouse. Thereafter a designated amount of the test compound, which had been formulated into an emulsifiable concentrate according to Formulation Example 2 and diluted with water containing a spreading agent comparable to 10 liters per are, was sprayed by a small sprayer over the top of weeds to effect the foliar treatment equally on the whole surface. At this time, the growth condition of the weeds was that the height of grass was 20 to 30 cm at 6 to 8 leaf stages. After treatment, the weed was cultivated for 28 days in a greenhouse, and the herbicidal activity on the terrestrial part and the subterranean tuber of Purple nutsedge (Hamasuge) was examined. The results are shown in Table 6.

TABLE 6

| Test compound | Dosage of active ingredient (g/a) | Herbicidal activity | |
|---|---|---|---|
| | | Subterranean tuber of Purple nutsedge | Terrestrial part of Purple nutsedge |
| (1) | 80 | 4 | 3 |
| (2) | 80 | 4 | 3 |
| (3) | 80 | 4 | 3 |
| (4) | 80 | 4 | 3 |
| (5) | 80 | 4 | 3 |
| (7) | 80 | 4 | 3 |
| (10) | 80 | 4 | 3 |
| (18) | 80 | 4 | 3 |
| (19) | 80 | 4 | 3 |
| (20) | 80 | 4 | 3 |
| (21) | 80 | 4 | 3 |
| (22) | 80 | 4 | 3 |
| A | 80 | 0 | 0 |

TEST EXAMPLE 5

Foliar treatment, plowed field.

Cylindrical plastic pots of diameter-10 cm, height-10 cm were filled with a soil of a plowed pg,19 field and tubers of Purple nutsedge (Hamasuge) and Yellow nutsedge were transplanted and Common ragweed (Butakusa) was sowed. The weeds were cultivated for 35 days in a greenhouse. Thereafter a designated amount of the test compound, which had been formulated into a liquid composition according to Formulation Example 5 and diluted with water containing a spread agent comparable to 5 liters per are, was sprayed by a smaller sprayer over the top of weeds to effect the foliar treatment equally on the whole surface. At this time, the growth conditions of weeds were that the

TABLE 5

| Test compound | Dosage of active ingredient (g/a) | Herbicidal activity | | | | | | | | | | |
|---|---|---|---|---|---|---|---|---|---|---|---|---|
| | | Corn | Cotton | Sugar beet | Oats | Johnson-grass | Japanese millet | Large crabgrass | Green foxtail | Common cocklebur | Velvetleaf | Tall morningglory |
| (1) | 80 | — | — | — | 5 | 5 | 5 | 5 | 5 | 5 | 5 | 5 |
| | 20 | 0 | 0 | 1 | 5 | 5 | — | — | 5 | 4 | 5 | — |
| (2) | 80 | — | 1 | — | 5 | 5 | 5 | 4 | 5 | 5 | 5 | 5 |
| | 20 | 0 | 0 | — | 4 | — | — | — | 4 | 5 | 4 | 4 |
| (3) | 80 | — | — | 1 | 5 | — | 5 | — | 4 | 5 | 5 | — |
| | 20 | 0 | 0 | 0 | 5 | — | — | — | — | 5 | 4 | — |
| A | 80 | 0 | 0 | 0 | 0 | 0 | 0 | 0 | 0 | 0 | 0 | 0 |

TEST EXAMPLE 4

Foliar treatment, plowed field, perennial weeds.

height of grass was 25 to 35 cm at 6 to 9 leaf stages. After treatment, the weeds were cultivated for 28 days in a greenhouse, and the herbicidal activity on the terrestrial part of the weeds and the subterranean tuber of Purple nutsedge was examined. The results are shown in Table 7.

TABLE 7

| Test compound | Dosage of active ingredient (g/a) | Herbicidal activity | | | |
| --- | --- | --- | --- | --- | --- |
| | | Terrestrial part of Purple nutsedge | Subterranean tuber of Purple nutsedge | Terrestrial part of Yellow nutsedge | Common ragweed |
| 18 | 80 | 4 | 4 | 4 | 4 |
|    | 40 | 4 | 4 | 4 | — |
|    | 20 | 3 | 4 | — | — |
| A  | 80 | 1 | 0 | 0 | 2 |

We claim:

1. A method for controlling the growth of undesired weeds which comprises applying a herbicidally effective amount of a herbicidal composition which comprises as an essential active ingredient a compound of the formula:

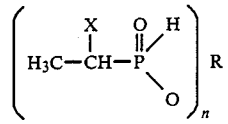

wherein X is a hydroxyl group or a hydroxylamino group, R is a hydrogen atom, an inorganic counter cation, an organic counter cation or an ester residue, and n is an integer of 1 to 3, and an inert carrier or diluent, to the area where the weeds grow or will grow.

2. The method according to claim 1, wherein the herbicide is applied by foliar or soil treatment.

3. The method of claim 1, wherein the undesired weeds are selected from the group consisting of broad-leaved weeds, gramineous weeds, and Cyperaceous weeds.

4. The method of claim 1, wherein the area is selected from the group consisting of a cornfield, a cotton field, and a sugar beet field.

5. The method of claim 1, wherein the area is selected from the group consisting of an orchard, a forest, and a non-agricultural field.

* * * * *